(12) United States Patent
Glushakov et al.

(10) Patent No.: US 11,069,447 B2
(45) Date of Patent: Jul. 20, 2021

(54) SYSTEMS AND METHODS FOR TOPOLOGY-BASED CLINICAL DATA MINING

(71) Applicant: Intego Group, LLC, Maitland, FL (US)

(72) Inventors: Sergey Glushakov, Orlando, FL (US); Vladimir Balon, Winter Park, FL (US); Iryna Kotenko, Kharkov (UA); Andriy Rekalo, Kharkov (UA); Kostiantyn Drach, Bremen (DE); Bogdan Chornomaz, Nashville, TN (US); Victoriia Shevtsova, Kharkov (UA)

(73) Assignee: INTEGO GROUP, LLC, Maitland, FL (US)

( * ) Notice: Subject to any disclaimer, the term of this patent is extended or adjusted under 35 U.S.C. 154(b) by 249 days.

(21) Appl. No.: 16/147,640

(22) Filed: Sep. 29, 2018

(65) Prior Publication Data

US 2020/0105421 A1    Apr. 2, 2020

(51) Int. Cl.
| | | |
|---|---|---|
| *G16H 50/70* | (2018.01) | |
| *G06K 9/62* | (2006.01) | |
| *G06N 20/00* | (2019.01) | |
| *G06F 16/904* | (2019.01) | |
| *G06F 16/901* | (2019.01) | |
| *G06F 16/9038* | (2019.01) | |

(52) U.S. Cl.
CPC ........... *G16H 50/70* (2018.01); *G06F 16/904* (2019.01); *G06F 16/9024* (2019.01); *G06F 16/9038* (2019.01); *G06K 9/6248* (2013.01); *G06N 20/00* (2019.01); *G06F 2216/03* (2013.01)

(58) Field of Classification Search
CPC ... G16H 50/70; G06F 16/904; G06F 16/9024; G06F 16/9038; G06F 2216/03; G06N 20/00; G06K 9/6248
USPC ........................................................ 707/776
See application file for complete search history.

(56) References Cited

U.S. PATENT DOCUMENTS

| | | | |
|---|---|---|---|
| 8,443,013 B1* | 5/2013 | Lin | G06Q 10/04 707/810 |
| 9,330,127 B2* | 5/2016 | Steinberg | G06N 5/022 |
| 2007/0174252 A1* | 7/2007 | Rawlings | G16H 15/00 |
| 2008/0097938 A1* | 4/2008 | Guyon | G06K 9/6231 706/12 |

(Continued)

*Primary Examiner* — Hicham Skhoun
(74) *Attorney, Agent, or Firm* — Georgiy L. Khayet

(57) ABSTRACT

Methods and systems for topology-based clinical data mining are provided. An example system includes a pre-processing module to process the clinical datasets to generate a table of outcomes and a table of predictors of trial subjects. The system includes a graph construction module to generate metric graphs based on the table of outcomes. The metric graphs include nodes representing the subjects and edges selectively connecting the nodes according to pre-determined criteria. The graph construction module may select a graph of interest from the metric graphs and generate a compressed version of the graph of interest. The system may further include an interactive visualization module to display a graphical representation of the graph of interest or the compressed version, receive selection of groups of the trial subjects, automatically highlight groups of related subjects, and perform, using the table of predictors, a statistical analysis of predictors of subjects within the selected groups.

20 Claims, 9 Drawing Sheets

(56) References Cited

U.S. PATENT DOCUMENTS

| | | | |
|---|---|---|---|
| 2014/0278754 A1* | 9/2014 | Cronin | G06F 16/2453 705/7.29 |
| 2014/0297642 A1* | 10/2014 | Lum | G06F 16/90328 707/737 |
| 2015/0127650 A1* | 5/2015 | Carlsson | G06F 16/93 707/737 |
| 2016/0034561 A1* | 2/2016 | Sexton | G06F 16/9024 707/737 |
| 2016/0350389 A1* | 12/2016 | Kloke | G06F 16/9024 |
| 2017/0046422 A1* | 2/2017 | Tan | G06F 16/2471 |
| 2020/0167694 A1* | 5/2020 | Pisner | G06F 16/9024 |

* cited by examiner

Process, by a pre-processing module, clinical datasets to generate a first table, the first table comprising first rows representing trial subjects and first columns including outcomes of the trial subjects, and a second table, the second table comprising second rows representing the trial subjects and second columns including predictors of the trial subjects
705

Generate, by a graph construction module and based on the first table, one or more metric graphs, the one or more metric graphs including nodes and edges, wherein the nodes represent the trial subjects and the edges selectively connect the nodes according to one or more pre-determined criteria
710

Select, by the graph construction module, a graph of interest from the one or more metric graphs
715

Generate, by the graph construction module, a compressed version of the graph of interest, the compressed version including a clustered graph
720

Generate, by the graph construction module, a first layout of the graph of interest and a second layout of the compressed version of the graph of interest, the first layout and the second layout being visually aligned
725

```
┌─────────────────────────────────────────────────────────────────┐
│ Display, by an interactive visualization module and based on the first layout or
│ the second layout, a graphical representation of the graph of interest
│ 730
└─────────────────────────────────────────────────────────────────┘
                                  ↓
┌─────────────────────────────────────────────────────────────────┐
│ Assign, by the interactive module, colors to the nodes of the graph of interest,
│ wherein the colors are based on a selected outcome or a selected predictor
│ 735
└─────────────────────────────────────────────────────────────────┘
                                  ↓
┌─────────────────────────────────────────────────────────────────┐
│ Perform, by the interactive module and using one or more machine learning
│ algorithms, an automatic search to identify at least one group of related trial
│ subjects
│ 740
└─────────────────────────────────────────────────────────────────┘
                                  ↓
┌─────────────────────────────────────────────────────────────────┐
│ Highlight, by the interactive module, nodes in the graphical representation, the
│ nodes corresponding to the related trial subjects
│ 745
└─────────────────────────────────────────────────────────────────┘
                                  ↓
┌─────────────────────────────────────────────────────────────────┐
│ Receive, by the interactive visualization module and via the graphical
│ representation, a user input, the user input including one or more selected
│ groups of the trial subjects
│ 750
└─────────────────────────────────────────────────────────────────┘
                                  ↓
┌─────────────────────────────────────────────────────────────────┐
│ Perform, by the interactive visualization module configured to use the second
│ table, a statistical analysis of predictors associated with trial subjects within the
│ one or more selected groups of the trial subjects
│ 755
└─────────────────────────────────────────────────────────────────┘
                                  ↓
┌─────────────────────────────────────────────────────────────────┐
│ Display, by the interactive visualization module, results of the statistical
│ analysis
│ 760
└─────────────────────────────────────────────────────────────────┘
```

*FIG. 7*
*(Continued)*

SYSTEMS AND METHODS FOR TOPOLOGY-BASED CLINICAL DATA MINING

TECHNICAL FIELD

This disclosure generally relates to clinical data processing. More specifically, this disclosure relates to systems and methods for topology-based clinical data mining.

BACKGROUND

Clinical trials are designed and conducted to study the safety and efficacy of biomedical or behavioral interventions. Typically, only a relatively small fraction of the data collected during clinical trials is used by investigators to demonstrate the safety and efficacy of a medical intervention. However, clinical trials generate significant amounts of data that can be subsequently explored to identify unexpected factors that influence the outcomes of interest and lead to new hypotheses.

Performing a comprehensive analysis of a clinical trial dataset can be challenging. While most approaches to mining clinical data focus on univariate relationships between a specific outcome and a few predictive variables, there is a lack of data integration and visualization tools that can improve understanding of the entire dataset. Examining clinical data with a focus on a specific single outcome in isolation from other factors may lead to an incomplete, or even misleading, view of complex settings. Standard biostatistical methods can be used as technical tools to confirm (or refute) the hypotheses generated by an investigator and, therefore, depend on the researcher's ability to develop solid hypotheses. However, in the case of clinical trial datasets, the number of possible hypotheses to explore is very large, and it can be very difficult to select the most relevant.

SUMMARY

This section introduces a selection of concepts in a simplified form that are further described in the Detailed Description section, below. This summary does not identify key or essential features of the claimed subject matter and is not intended to be an aid in determining the scope of the claimed subject matter.

The methods and systems presented in this disclosure are directed to topology-based clinical data mining. Embodiments of the present disclosure may also provide an integrated approach that combines clinical biostatistics, topological data analysis, machine learning, and data visualization. The present technology may allow mining for hidden patterns in clinical datasets. Some embodiments of the present disclosure provide an interactive visualization application allowing researchers to explore groups of trial subjects with similar outcomes and perform statistical analysis of predictors of a trial subject within the groups.

According to one embodiment of this disclosure, there is provided a system for topology-based clinical data mining. A system may include a pre-processing module configured to process the clinical datasets to generate a first table and a second table. The first table may include first rows representing trial subjects and first columns including outcomes of the trial subjects. The second table may include the second rows representing the trial subjects and second columns including predictors of the trial subjects.

The system may include a graph construction module configured to generate, based on the first table, one or more metric graphs. The metric graphs may include nodes and edges. The nodes represent the trial subjects and the edges selectively connect the nodes according to one or more pre-determined criteria. The pre-determined criteria may include a determination that a distance between the data points corresponding to trial subjects does not exceed a pre-determined distance threshold. The data points may include vectors of outcomes of the trial subjects' nodes. The distance may include one of a Euclidean distance, a normalized Euclidean distance, a Manhattan distance, a Hamming distance, and a Gower distance.

The graph construction module can be further configured to select a graph of interest from the metric graphs. The graph construction module may further generate a compressed version of the graph of interest. The compressed version of the graph of interest may represent a clustered graph where nodes correspond to groups of trial subjects. The graph construction module may further generate a first layout of a graph of interest and a second layout of the compressed version of the graph of interest.

The system may further include an interactive visualization module configured to display, based on the first layout or the second layout, a graphical representation of the graph of interest. The interactive visualization module can be further configured to receive, via the graphical representation, a user input. The user input may include one or more selected groups of the trial subjects. The interactive visualization module may be also configured to perform an automatic search to highlight a group of related trial subjects (in terms of pre-defined outcomes) in the graph of interest. The automatic search can be based on one or more machine-learning algorithms. The interactive visualization module can be further configured to perform, using the second table, a statistical analysis of predictors associated with trial subjects within the selected groups of the trial subjects and display a report with a result of the statistical analysis.

The outcomes may include biomarkers, vital signs, results of physiological measurements, and questionnaire items. The predictors may include one or more demographic attributes, medical history attributes, and medical interventions attributes. The pre-processing module can be configured to normalize data in the clinical datasets. The pre-processing module can be configured to fill in missing values for the outcomes in the first table. The pre-processing module can be configured to generate, based on the clinical datasets, one or more synthetic variables. The synthetic variables may include a combination of one or more outcomes associated with trial subjects.

The graph construction module can be configured to determine a graph with the highest value of an objective function. The objective function maps a set of metric graphs to real numbers. The graph construction module may select the graph with a highest value of the objective function as the graph of interest. The objective function may include a projection-driven modularity of a metric graph.

The statistical analysis includes calculating p-values for the statistical tests to determine whether a distribution of the predictor values of trial subjects within a first group from the one or more selected groups is different from a distribution of the predictor values for the trial subjects within a second group from the one or more selected groups. The statistical analysis may also include calculating p-values for the statistical tests to determine whether a distribution of the predictor values for the trial subjects within one of the one or more selected groups is different from a distribution of the predictor values for the rest of trial subjects within the clinical datasets.

The interactive visualization module can be configured to receive a further user input. The further user input may include a selected predictor from the predictors or a selected outcome from the outcomes. The interactive visualization module can be configured to assign colors to nodes of the graphs of interest. The colors can encode numerical values for the selected predictor or the selected outcome. The colors encoding can be represented by a color palette bar. Prior to selection of an outcome or predictor, the colors of the nodes can be determined based on projection values of data points, wherein the data points include vectors of the outcomes of the trial subjects corresponding to the nodes.

According to another embodiment of this disclosure, the method for topology-based clinical data mining is provided. The method can be implemented by computer hardware, software, or any variations thereof.

The method may include processing, by a pre-processing module, the clinical datasets to generate a first table and a second table. The first table may include first rows representing trial subjects and first columns including outcomes of the trial subjects. The second table may include second rows representing the trial subjects and second columns including predictors of the trial subjects. The method may further include generating, by a graph construction module and based on the first table, one or more metric graphs. The metric graphs may include nodes and edges, wherein the nodes represent the trial subjects and the edges selectively connecting the nodes according to one or more pre-determined criteria. The method may further include selecting, by the graph construction module, a graph of interest from the metric graphs. The method may further include generating a compressed version of the graph of interest. The compressed version may include a clustered graph. The method may further include generating, by the graph construction module, a first layout of the graph of interest and a second layout of the compressed version of the graph of interest. The first layout and the second layout can be visually aligned.

The method may further include displaying, by an interactive visualization module and based on the first layout or the second layout, a graphical representation of the graph of interest. The method may further include receiving, by the interactive visualization module, a user input. The user input may include one or more selected groups of the trial subjects. The method may further include performing an automatic search to identify groups of related trial subjects (in terms of pre-defined outcomes) and highlight the nodes representing the related trial subjects in the graph of interest. The method may further include performing, by the interactive visualization module and using the second table, a statistical analysis of predictors associated with trial subjects within the selected groups. The method may further include displaying, by the interactive visualization module, a report with results of the statistical analysis.

In another example, the method for topology-based clinical data mining may be implemented by a series of computer-executable instructions residing on a transitory or non-transitory storage medium such as a disk drive or computer-readable medium.

Additional objects, advantages, and novel features of the examples will be set forth in part in the description which follows, and in part will become apparent to those skilled in the art upon examination of the following description and the accompanying drawings or may be learned by production or operation of the examples. The objects and advantages of the concepts may be realized and attained by means of the methodologies, instrumentalities, and combinations particularly pointed out in the appended claims.

BRIEF DESCRIPTION OF THE DRAWINGS

Embodiments are illustrated by way of example and not limitation in the figures of the accompanying drawings, in which like references indicate similar elements and in which:

FIG. 6 shows a screen of an interactive visualization module, according to an example embodiment.

FIG. 7 is a flow chart showing a method for topology-based clinical data mining, according to an example embodiment.

DETAILED DESCRIPTION OF EXAMPLE EMBODIMENTS

Figure 1:
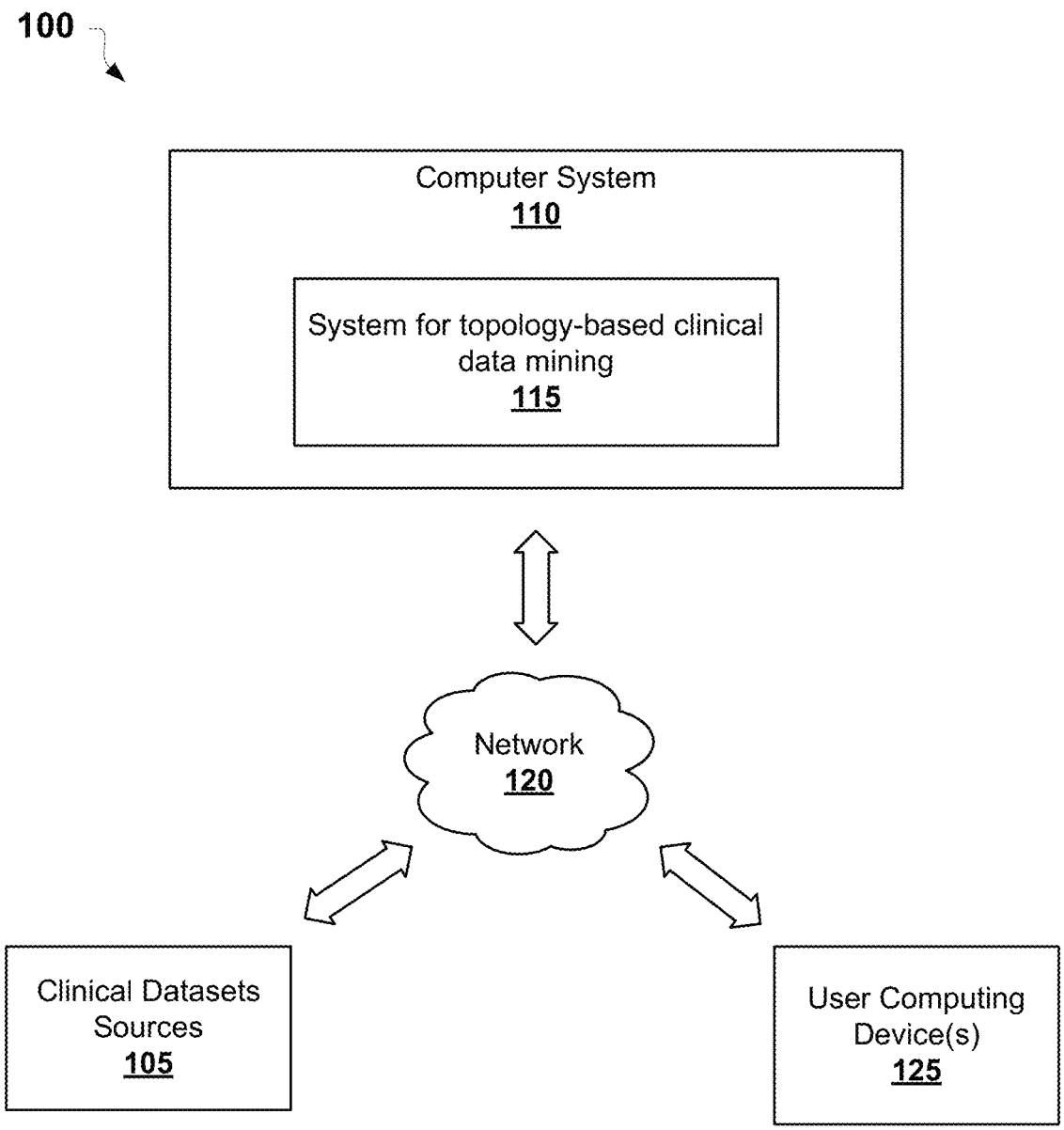
FIG. 1 is a block diagram showing an example architecture, wherein methods for topology-based clinical data mining can be implemented.

The following detailed description of embodiments includes references to the accompanying drawings, which form a part of the detailed description. Approaches described in this section are not prior art to the claims and are not admitted to be prior art by inclusion in this section. The drawings show illustrations in accordance with example embodiments. The embodiments can be combined, other embodiments can be utilized, or structural, logical and operational changes can be made without departing from the scope of what is claimed. The following detailed description is, therefore, not to be taken in a limiting sense, and the scope is defined by the appended claims and their equivalents.

Embodiments of this disclosure are concerned with methods and systems for topology-based clinical data mining. The methods described herein can be implemented by hardware modules, software modules, or a combination of both. The methods can also be embodied in computer-readable instructions stored on computer-readable media. As should be evident from the following description, the methods and systems of this disclosure allow mining for hidden patterns in clinical datasets. Embodiments of the present disclosure may also provide an interactive visualization application allowing researchers to explore groups of trial subjects with similar outcomes and perform statistical analysis of predictors of trial subjects within the groups.

The embodiments will now be presented with reference to the accompanying drawings. These embodiments are described and illustrated by various modules, blocks, components, circuits, steps, operations, processes, algorithms, and the like, collectively referred to as "components" for simplicity. These components may be implemented using electronic hardware, computer software, or any combination thereof. Whether such components are implemented as hardware or software depends upon the particular application and design constraints imposed on the overall system. By way of example, a component, or any portion of a component, or any combination of components may be implemented with a "processing system" that includes one or more processors. Examples of processors include microprocessors, microcontrollers, Central Processing Units (CPUs), digital signal processors (DSPs), field programmable gate arrays (FPGAs), programmable logic devices (PLDs), state machines, gated logic, discrete hardware circuits, and other suitable hardware configured to perform various functions described throughout this disclosure. One or more processors in the processing system may execute software, firmware, or middleware (collectively referred to as "software"). The term "software" shall be construed broadly to mean instructions, instruction sets, code, code segments, program code, programs, subprograms, software components, applications, software applications, software packages, routines, subroutines, objects, executables, threads of execution, procedures, functions, and the like, whether referred to as software, firmware, middleware, microcode, hardware description language, or otherwise. The software may be stored on or encoded as one or more instructions or code on a non-transitory computer-readable medium. Computer-readable media includes computer storage media. Storage media may be any available media that can be accessed by a computer. By way of example, and not limitation, such computer-readable media can comprise a random-access memory (RAM), a read-only memory (ROM), an electrically erasable programmable ROM (EEPROM), compact disk ROM (CD-ROM) or other optical disk storage, magnetic disk storage, solid state memory, or any other data storage devices, combinations of the aforementioned types of computer-readable media, or any other medium that can be used to store computer executable code in the form of instructions or data structures that can be accessed by a computer.

For purposes of this document, the terms "or" and "and" shall mean "and/or" unless stated otherwise or clearly intended otherwise by the context of their use. The term "a" shall mean "one or more" unless stated otherwise or where the use of "one or more" is clearly inappropriate. The terms "comprise," "comprising," "include," and "including" are interchangeable and not intended to be limiting. For example, the term "including" shall be interpreted to mean "including, but not limited to."

The term "module" shall be construed to mean a hardware device, software, or a combination of both. For example, a hardware-based module can use either one or more microprocessors, application-specific integrated circuits (ASICs), programmable logic devices, transistor-based circuits, or various combinations thereof. Software-based modules can constitute computer programs, computer program procedures, computer program functions, and the like. In addition, a module of a system can be implemented by a computer or server, or by multiple computers or servers connected into a network. Hardware or software implementations can depend on particular system implementation and constraints. For example, a communication module may include a radio modem, Ethernet module, network interface, communication port, or circuit terminals. In other embodiments, a communication module may include software, software procedure, or software-based function configured to receive and transmit data by a hardware device, such as a processor. Other implementations of communication module can involve programmable and non-programmable microcontrollers, processors, circuits, computing devices, servers, and the like.

The terms "topological data map", "data map", and "graph" shall be construed to mean the same and refer to the visual representation of individual trial subjects or groups of trial subjects by nodes connected with edges.

The terms "trial subject", "study subject", "human subject", and "subject" shall be construed to mean the same and refer to an individual who is the source of data for a research investigator through intervention or interaction with the individual or from individually identifiable information. Such individuals can include healthy humans or patients.

Referring now to the drawings, exemplary embodiments are described. The drawings are schematic illustrations of idealized example embodiments. Thus, the example embodiments discussed herein should not be construed as limited to the particular illustrations presented herein, rather these example embodiments can include deviations and differ from the illustrations presented herein.

FIG. 1 is a block diagram showing an example architecture 100 suitable for implementing methods for topology-based clinical data mining, according to some example embodiments. The architecture 100 may include one or more clinical datasets sources 105, a computer system 110, one or more user computing device(s) 125, and a network 120.

The clinical datasets sources 105 may include server(s) configured to store and provide access to clinical datasets. The clinical datasets can be formatted according to a standard format (for example, a Clinical Data Interchange Standards Consortium (CDISC) format, a Study Data Tabulation Model (SD™) format, an analysis data model (ADaM) format, and the like).

The computer system 110 may include a standalone server or cloud-based computing resource(s). The standalone server or the cloud-based computing resource(s) can be shared by multiple users. The cloud-based computing resource(s) can include hardware and software available at a remote location and accessible over the network 120. The cloud-based computing resource(s) can be dynamically reallocated based on demand. The cloud-based computing resources may include one or more server farms/clusters including a collection of computer servers which can be co-located with network switches and/or routers. The computer system 110 may include a system 115 for topology-based clinical data mining.

The one or more user computing device(s) 125 may include a personal computer, a laptop computer, tablet computer, smartphone, server computer, network storage computer, or any other computing device comprising at least networking and data processing capabilities.

The network 120 may include any wired, wireless, or optical networks including, for example, the Internet, intranet, local area network (LAN), Personal Area Network (PAN), Wide Area Network (WAN), Virtual Private Network (VPN), cellular phone networks (e.g., Global System for Mobile (GSM) communications network, packet switching communications network, circuit switching communications network), Bluetooth radio, Ethernet network, an IEEE 802.11-based radio frequency network, a Frame Relay network, Internet Protocol (IP) communications network, or any other data communication network utilizing physical layers, link layer capability, a network layer to carry data packets, or any combinations of the above-listed data networks.

Users of the user computing device(s) 125 may access the system 115 using one or more applications of the client device, for example a web browser, via the network 120. The users may configure the system 115 by selecting clinical datasets and indicating parameters for construction of graphs representing the data in clinical datasets. The system 115 may be further configured to display a graphical representation of the graphs and provide users with a means for selecting groups of trial subjects using the graphical representation. The system 115 may further perform a statistical analysis of predictors of trial subjects within the selected groups. The system 115 may further display the results of statistical analysis.

Figure 2:
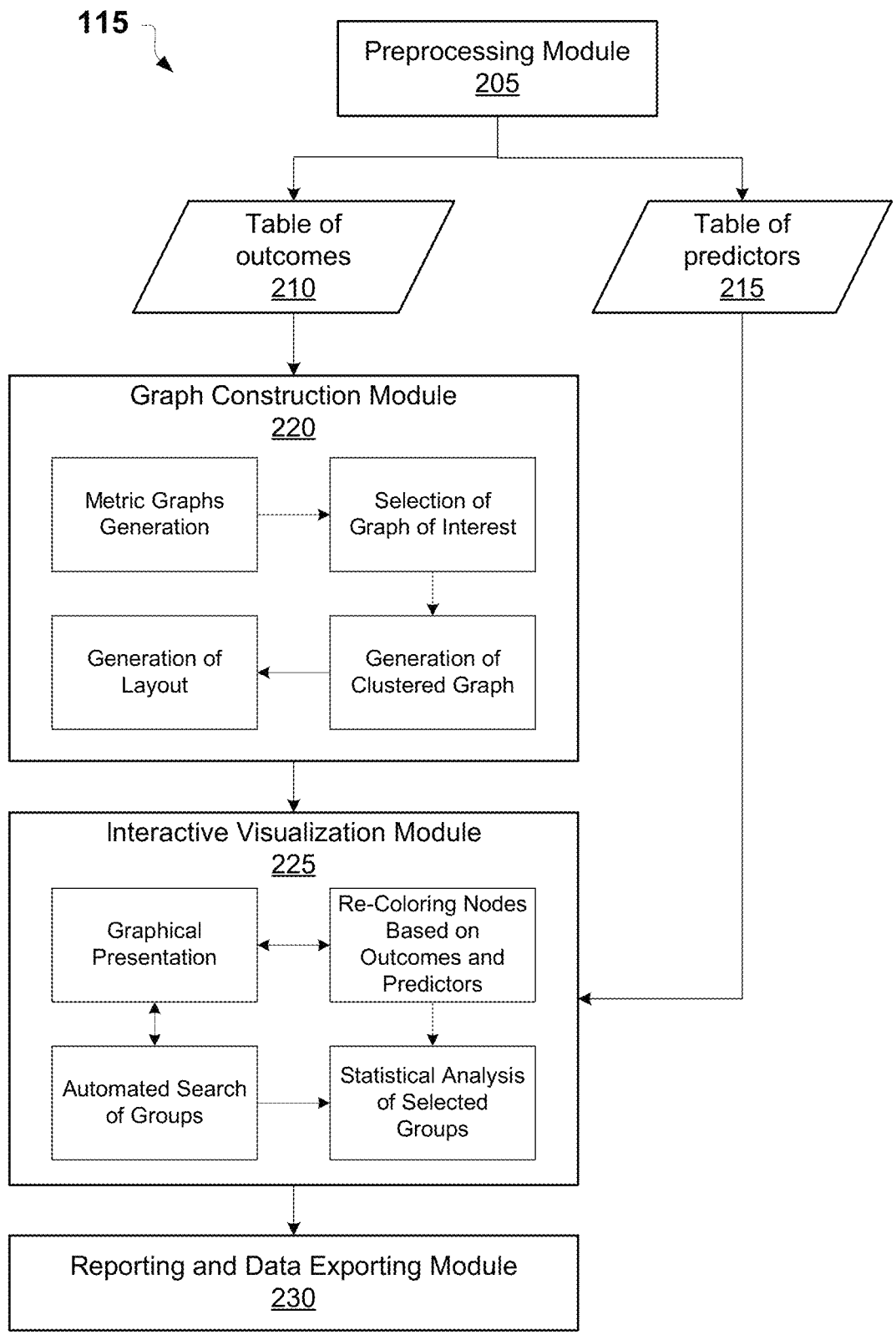
FIG. 2 is a block diagram showing a system for topology-based clinical data mining, according to one example embodiment.

FIG. 2 is a block diagram showing an example system 115 for topology-based clinical data mining, according to some example embodiments. The system 115 may include a preprocessing module 205, a graph construction module 220, an interactive visualization module 225, and a reporting and data exporting module 230.

The preprocessing module 205 may be configured to transform original clinical datasets into a table 210 of outcomes and a table of 215 of predictors. The table 210 may include rows representing trial subjects and columns representing outcomes. The outcomes (also known as response variables) may include biomarkers, results of measurement of vital signs, results of physiological measurements, and questionnaire items recorded during medical treatment of trial subjects. Examples of the outcomes are levels of serum creatinine, blood urea nitrogen, and neutrophil gelatinase-associated lipocalin as a means of evaluating kidney function, absolute or percentage change in the tumor size over the course of study, quality of life score and so forth. The outcome may include questionnaire item to assess trial subject's general health or quality of life, and the like.

The table 215 may include rows corresponding to the trial subjects and predictors associated with the trial subjects. The predictors may include, for example, demographic attributes, such as sex, age, ethnicity, and residence. The predictors may also include medical history attributes and medical interventions attributes.

The clinical datasets can include quantitative data, binary data, or categorical data. The preprocessing module 205 may transform the categorical data into numerical values. For example, an "emotional level" can be represented by numbers of 1 to 7. One of the main problems of clinical datasets is missing values. Therefore, the preprocessing module 205 can be configured to fill in missing values for outcomes in table 210. The preprocessing module 205 can be also configured to combine one or more variables of the clinical data to synthetic variables to aggregate more data for an analysis.

The preprocessing module 205 can be further configured to normalize the values of outcomes to facilitate measurement of distances between data points to find similarities in the clinical datasets. Data points may include row vectors $\{x=(x_1, x_2, \ldots, x_n)\}$, wherein each vector corresponds to a single trial subject x, and $x_i$ denotes the i-th outcome for the trial subject x.

The graph construction module 220 can be configured to generate, based on the table 210 of outcomes, one or more metric graphs (also referred to as "topological data map" or "data map"). In each of the metric graphs, a single node corresponds to an individual trial subject. If two nodes represent similar trial subjects (in terms of pre-defined outcomes), they are connected with an edge. To determine whether two trial subjects are similar, a distance between two data points representing the two trial subjects can be calculated according to a distance function. If the distance does not exceed a distance threshold, then the two nodes (representing the two trial subjects) are connected with an edge.

The construction of a metric graph may depend on a selection of outcomes to be considered when calculating the distance, a distance function to calculate the distance, and a distance threshold. By changing the selection of outcomes, the distance function and the distance threshold, substantial number of metric graphs can be generated.

If the data points represent purely quantitative data, a Euclidean distance, a normalized Euclidean distance, and a Manhattan distance can be used to calculate distances between the data points. A Hamming distance can be used to calculate a distance if the data points represent purely categorical data. If several outcomes of different types (quantitative, binary, categorical) are combined in the table of outcomes, then the data points represent mixed data (quantitative data and categorical data). When the data points represent mixed data, a more general measure of a distance, such as the Gower distance, can be used.

In some embodiments, prior to construction of the metric graphs, the data points $\{x=(x_1, x_2, \ldots, x_n)\}$ can be divided into overlapping subsets. During the construction of the metric graphs, a distance function and distance threshold can be selected independently for each of the overlapping subsets. To obtain the overlapping subsets, each data point $\{x=(x_1, x_2, \ldots, x_n)\}$ is mapped by a projection rule (referred to as a "projection") to the unique point in the set of points $\{p=(p_1, p_2, \ldots, p_m)\}$ (referred to as "the values of the projection" or "projection values"). The projections can be one-dimensional (corresponds to m=1) or multidimensional (corresponding to m>1). The values of the projections can be further divided into overlapping domains. The data points corresponding to one of the overlapping domains can be further collected into one of the overlapping subsets.

The graph construction module 220 can be further configured to select a graph of interest from the metric graphs. The graph of interest can be determined as the most representative metric graph. To determine the most representative and most stable graph, the graph construction module 220 can calculate values of one or more objective functions of the metric graphs. The objective functions map a set of metric graphs to real numbers. The metric graph having the highest value of one of the objective functions can be selected as the graph of interest. In some embodiments, the objective function may include a projection-driven modularity of the metric graphs. According to some embodiments of the present disclosure, a projection-driven modularity of a metric graph can be defined as a value that measures a difference between the metric graph and a random graph. The difference can be measured within each individual subgraph comprising nodes whose projection values fall into the same domain among the overlapping domains that were used to construct the metric graph.

The graph construction module 220 can be further configured to generate a clustered graph from the graph of interest. In the graph of interest, which is a metric graph, every node corresponds to a single trial subject while two nodes representing trial subjects (in terms of pre-defined outcomes) are connected with an edge. The clustered graph may represent a compressed version of the graph of interest. The compressed version can be obtained using one or more algorithms for clustering of nodes of graphs or community detection in graphs. For example, the compressed version of the graph of interest may include a clustered graph. Unlike the graph of interest (which is a metric graph), each node in the clustered graph corresponds to a group of trial subjects.

The clustering of a metric graph can be based on a modularity of groups of nodes in the metric graph. A cluster can be determined as a group of nodes of the metric graph, wherein the number of edges between nodes within the group is significantly more than the expected number of edges if the edges were distributed randomly within the graph. The modularity reflects a concentration of edges within the cluster in comparison to a random distribution of edges between all nodes in the metric graph according to a statistical model.

The graph construction module 220 can be further configured to generate layouts of the graph of interest in forms of a metric graph and a clustered graph. The layouts can be further used in graphical presentations of the graph of interest. Layout of the nodes of the clustered graph can be visually aligned with a layout of corresponding groups of nodes of the metric graph.

The interactive visualization module 225 can be configured to display a graphical representation of the graph of interest. A user may perform a visual exploration of the graph of interest to discover structural features. In some embodiments, the interactive visualization module 225 may provide a web-based interface for the user. The web-based interface may provide basic operations for visual exploration. The module 225 may display the graphical representation of the graph of interest in the form of a metric graph or a clustered graph based on a user selection. The interactive visualization module 225 may allow zooming in, zooming out, and panning of the graphical representation. The module 225 may provide an additional information for each node using a pop-up window when a user positions a mouse over the node. The module 225 may provide a means for selection of groups of nodes. For example, the module 225 may allow the user to select one or two groups of nodes of the graph of interest. The selected groups can be further used in statistical analysis of predictors associated with trial subjects in the selected groups.

The interactive visualization module 225 may be configured to color the nodes in the graphical representation of the graph of interest. The color of a node can be based on the value of one or more predictors or outcomes of a trial subject that the node represents. The color of a node can be based on a projections value of a data point. A user may re-color the nodes in the graphical representation by selecting a specific outcome or a specific predictor. The color of the nodes may highlight differences between a subgroup of trial subjects represented by a given region of the graphical representation and the rest of the trial subjects participating in a clinical trial, and, thereby, highlight patterns in the clinical datasets. The color of the nodes may also help the user to identify groups of trial subjects to be selected for statistical analysis.

The interactive visualization module 225 may be further configured to perform a statistical analysis of predictors related to trial subjects in the selected groups. In some embodiments, the user can select a region of the graph of interest to specify a group of trial subjects. Then statistical analysis can be performed to find predictors that explain why these trial subjects are combined into a group. After running statistical tests, a table of predictors with their corresponding p-values can be calculated to determine if a distribution of values of the predictors for the selected group of trial subjects is different from a distribution of values of the predictors of the rest of the trial subjects participating in the clinical study.

In some embodiments, the user can select a first region and a second region in the graph of interest, and, thus, select a first group of trial subjects and a second group of trial subjects. The module 225 may further perform calculations of p-values for the statistical tests to determine if a distribution of values of the predictor of the first group of trial subjects is different from a distribution of values of the predictor of the second group of trial subjects.

The interactive visualization module 225 may be also configured to perform an automatic search to highlight a group of related trial subjects in the graph of interest. The automatic search can be performed in addition to the visual inspection of the graph of interest that can be performed by a user. The automatic search can be carried out using machine learning algorithms for automated discovery of groups of trial subjects with common features and similarities.

The reporting and data exporting module 230 can be configured to allow a user to export data for the selected groups of trial subjects and generate one or more reports. The reports may include details of the statistical analysis in the form of a table and charts. The reports can be generated in a portable data format. The data concerning the selected groups of trial subjects may include a table of outcomes and predictors of the trial subjects in the selected group. The data can be exported in comma-separated values or other formats that are acceptable by external statistical analysis platforms. A user may use the exported data to determine other explanatory variables (predictors) that may be responsible for the similarities of responses observed within each selected group of the trial subjects who participated in clinical trial. An additional statistical analysis of the exported data can be performed using SAS™, R, or another data analytics platform.

Figure 3:
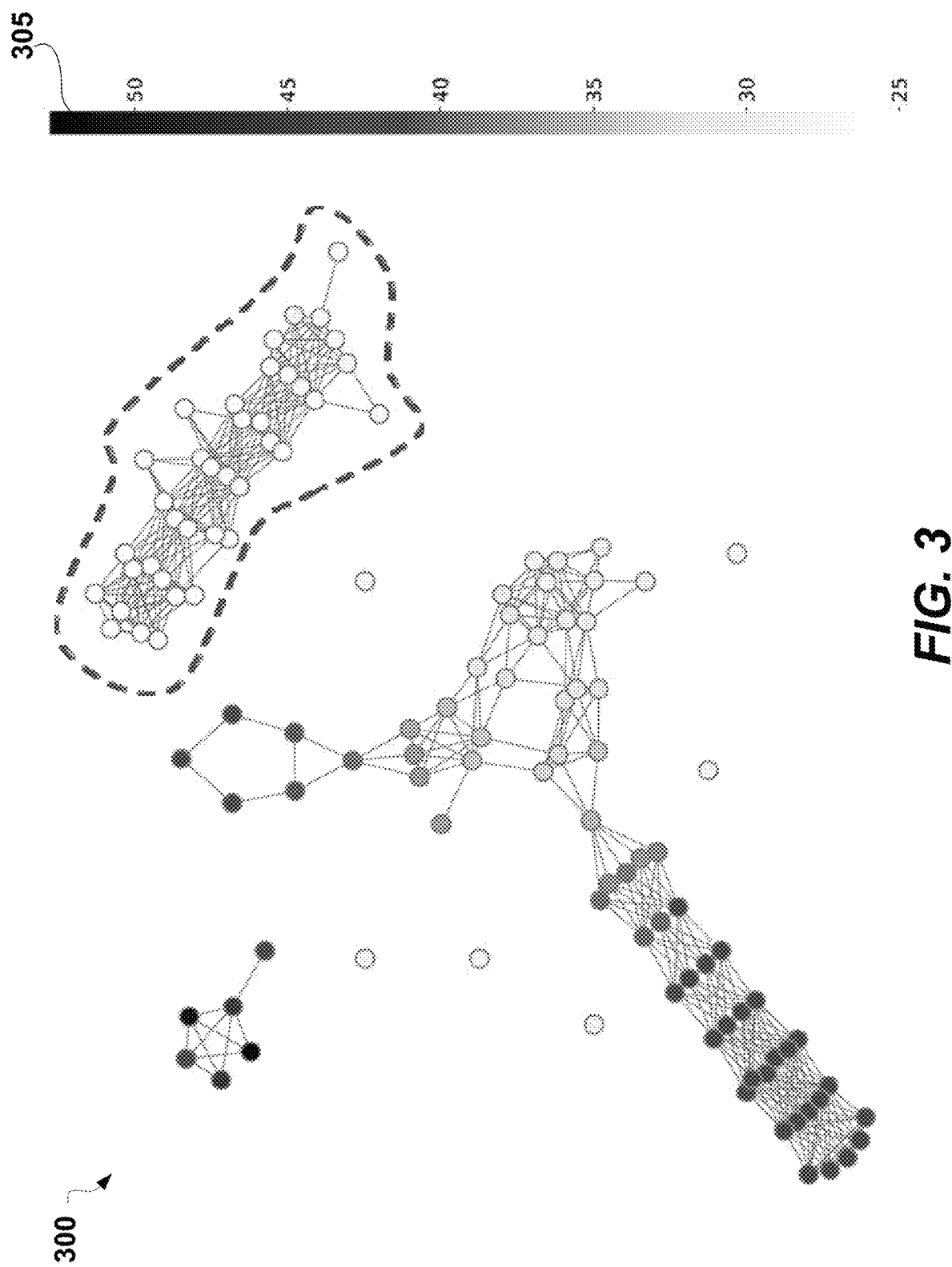
FIG. 3 is a plot of a metric graph, according to an example embodiment.

FIG. 3 shows a plot of an example metric graph 300, according to an example embodiment. Each node of the metric graph 300 represent a trial subject in a table of outcomes used to generate the metric graph. The nodes of the metric graph 300 are selectively connected. The nodes of the metric graph 300 are colored based on the value of a selected outcome or a selected predictor 305. Any group of the nodes can be selected for performing a statistical analysis of the predictors of the trial subjects within the groups.

Figure 4:
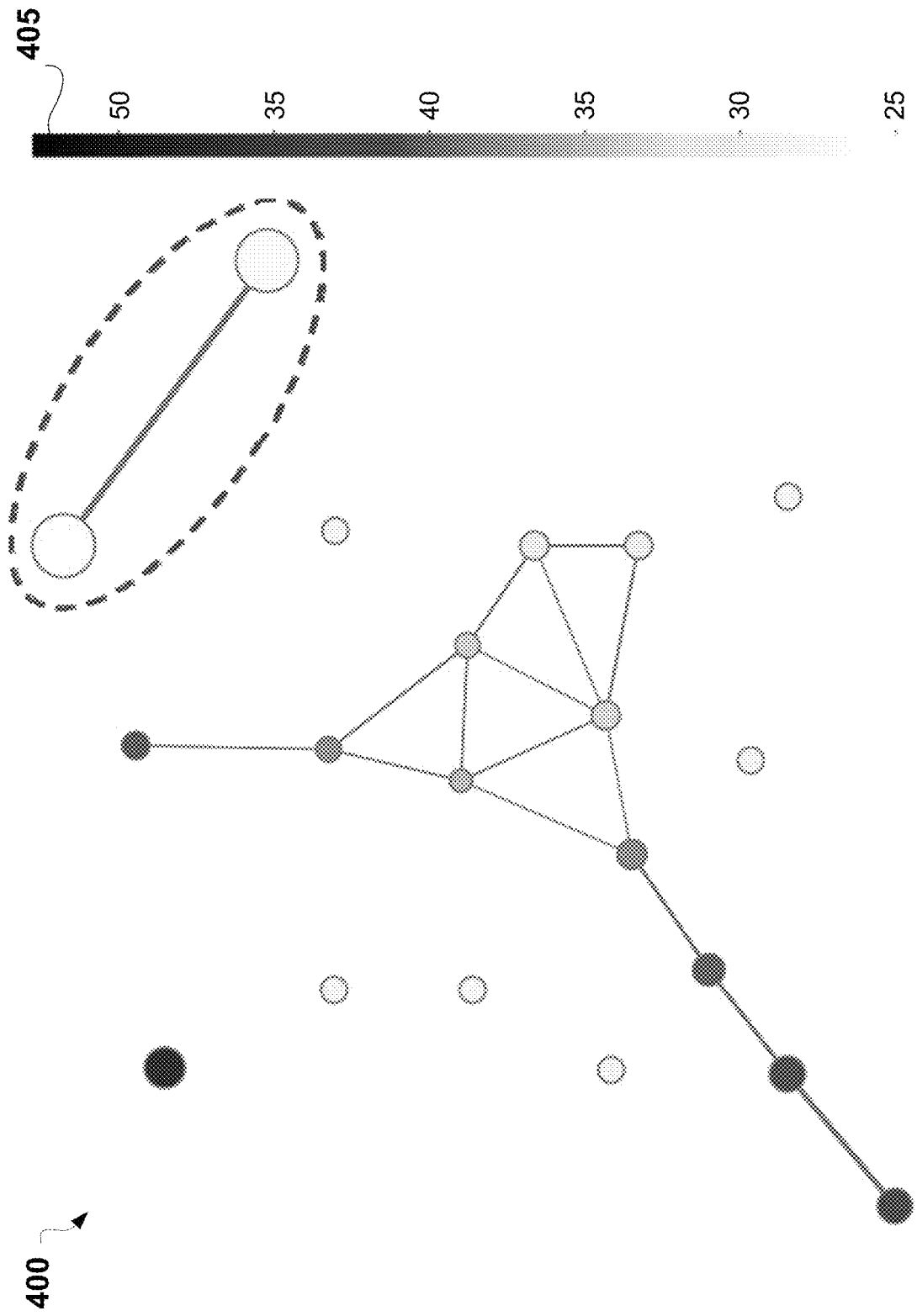
FIG. 4 is a plot of a clustered graph, according to an example embodiment.

FIG. 4 is a plot of a clustered graph 400, according to an example embodiment. Each node in the clustered graph 400 corresponds to a cluster of nodes in a metric graph. The color of a node in the clustered graph 400 can be based on a mean of values of a selected outcome or a selected predictor 405 for the trial subjects within the node.

Figure 5:
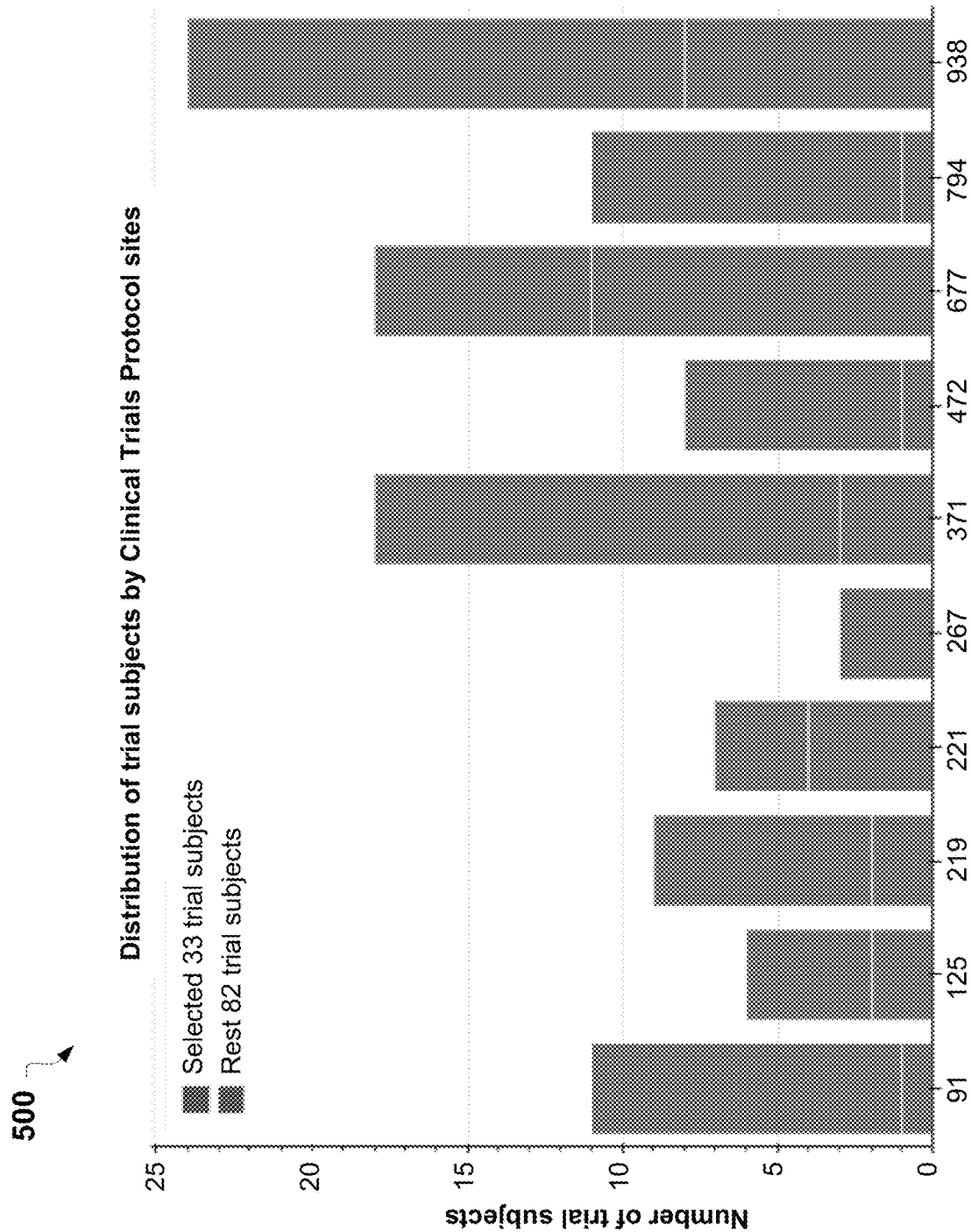
FIG. 5 is a chart diagram of distribution of trial subjects by a selected predictor for a selected group of trial subjects versus the rest of the trial subjects within clinical datasets, according to an example embodiment.

FIG. 5 is bar chart 500 of a distribution of trial subjects by a selected predictor for a selected group of trial subjects versus the rest of trial subjects, according to an example embodiment. In the example of FIG. 5, the selected predictor is the site at which clinical datasets are collected. Trial subjects from the selected group prevail in site 221 and site 677 while other clinical study sites exhibit the opposite pattern. This pattern may indicate that the distribution of trial subjects at site 221 and site 677 may result from, for example, a violation of a procedure for selecting of individuals to participate in the study, or a violation of a protocol of data collection for the individuals assigned to site 221 and site 677.

Figure 6:
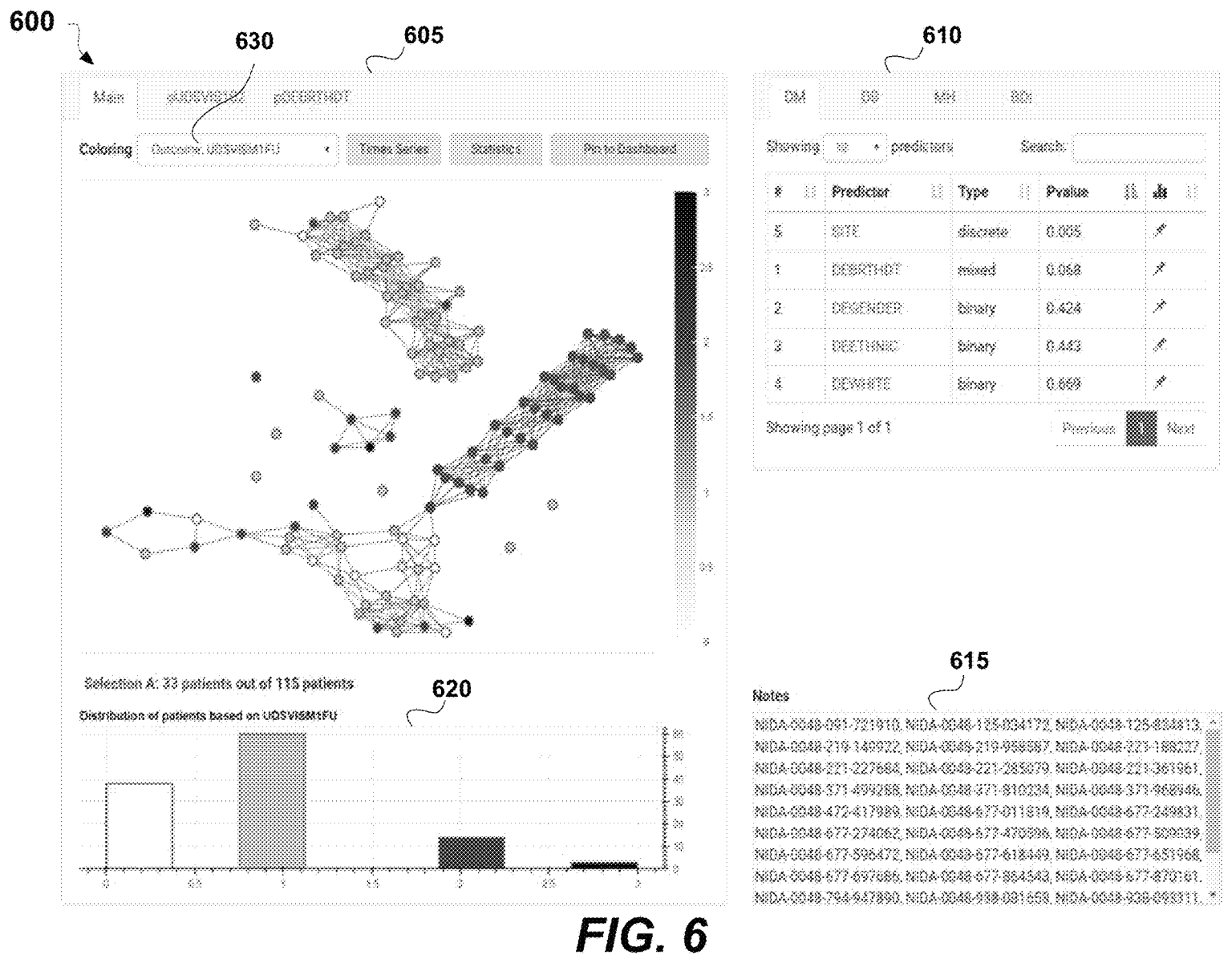

FIG. 6 shows a screen 600 of an interactive visualization module 225, according to an example embodiment. The screen 600 may include a window 605 showing a graphical presentation of a graph of interest in the form of a metric graph. Each node of the metric graph represents a single trial subject. The interactive visualization module 225 may allow a user to select a group of trial subjects in the graphical presentation. The nodes of the metric graphs are colored based on a value of an outcome selected in the field 630. The screen 600 may also include a plot 620 showing a distribution of trial subjects based on the value of an outcome or a predictor that was selected in the field 630.

The screen 600 may further include a table 610. The table 610 includes p-values for the statistical tests calculated to determine whether a distribution of values of the predictor for the trial subjects within selected group is different from a distribution of values for the predictor for the rest of trial subjects. In the example of FIG. 6, the predictors include a site at which clinical data are collected, birth date of a trial subject, gender of the trial subject, and ethnicity of the trial subject. The screen 600 may also show table 615 illustrating data related to the nodes of the metric graph displayed in window 605.

FIG. 7 is a process flow diagram showing a method 700 for topology-based clinical data mining, according to an example embodiment. The method 700 may be performed by processing logic that comprises hardware (e.g., decision-making logic, dedicated logic, programmable logic, ASIC, and microcode), software (such as software run on a general-purpose computer system or a dedicated machine), or a combination of both. The method 700 may have additional operations not shown herein, but which can be evident to those skilled in the art from the present disclosure. The method 700 may also have fewer operations than outlined below and shown in FIG. 7.

The method 700 may commence in block 705 with processing, by a pre-processing module, the clinical datasets to generate a first table and a second table. The first table may include first rows representing trial subjects and first columns including outcomes of the trial subjects. The second table may include second rows representing the trial subjects and second columns including predictors of the trial subjects. The outcomes may include biomarkers, vital signs, results of physiological measurements, and questionnaire items. The predictors may include one or more of demographic attributes, medical history attributes, and medical interventions attributes. The processing of the clinical datasets may include normalizing data in the clinical datasets, filling in missing values for the outcomes in the first table. The processing may include generating synthetic variables based on the data clinical datasets. The synthetic variables can represent a combination of one or more outcomes associated with trial subjects.

In block 710, the method 700 may generate, by a graph construction module and based on the first table, one or more metric graphs. The metric graphs include nodes and edges. The nodes represent the trial subjects and the edges selectively connect the nodes according to one or more pre-determined criteria. For example, the method 700 may calculate a distance between a first data point and a second data point. The first data point is a first vector $(x_1, x_2, \ldots, x_n)$ of outcomes of a first trial subject x represented by a first node. The second data point is a vector $(y_1, y_2, \ldots, y_n)$ of outcomes of a second trial subject y represented by a second node. The distance can be determined by a Euclidean distance, a normalized Euclidean distance, a Manhattan distance, a Hamming distance, or a Gower distance. The method 700 may determine that the distance is below a pre-determined value. Based on the determination, the method 700 may selectively connect the first node and the second node by an edge. A set of the metric graphs can be received by varying at least a selection of outcomes used to calculate the distance, distance function, and the distance threshold.

In block 715, the method 700 may select, by the graph construction module, a graph of interest from the one or more metric graphs. For example, the method 700 may determine a highest project-driven modularity graph from the one or more metric graphs and select the highest project-driven modularity graph as the graph of interest.

In block 720, the method 700 may generate, by the graph construction module, a compressed version of the graph of interest. The compressed version may include a clustered graph generated based on the graph of interest. The clustered graph may include one or more nodes, wherein the nodes represent groups of the trial subjects.

In block 725, the method 700 may generate, by the graph construction module, a first layout of the graph of interest and a second layout of the compressed version of graph of interest. The first layout and the second layout can be visually aligned during the generation.

In block 730, the method 700 may display, by an interactive visualization module and based on the first layout or the second layout, a graphical representation of the graph of interest.

In block 735, the method 700 may assign, by the interactive module, colors to the nodes of the graph of interest. The colors of the nodes can be based on a selected outcome or a selected predictor. The method 700 may receive the selected outcome or the selected predictor based on an user input via the interactive visualization module. The colors can be determined by values for the selected predictor or the selected outcome for the trial subjects corresponding to the nodes. Prior to selection of a predictor or an outcome, the colors of the nodes can be assigned based on projection values of data points, wherein the data points are vectors of outcomes of trial subjects corresponding to the nodes.

In block 740, the method 700 may perform, by the interactive module, an automatic search to identify at least one group of related trial subjects (in terms of pre-defined outcomes). The automatic search can be performed using one or more machine learning algorithms.

In block 745, the method 700 may highlight, by the interactive module, nodes corresponding to the related trial subjects in the graphical representation.

In block 750, the method 700 may receive a user input by the interactive visualization module and via the graphical representation. The user input may include one or more selected groups of the trial subjects. nodes In block 755, the method 700 may perform, by the interactive visualization module configured to use the second table, a statistical analysis of predictors associated with trial subjects within the one or more selected groups of the trial subjects. The statistical analysis may include calculating p-values for the statistical tests to determine whether a distribution of the predictor values of trial subjects within a first group from the one or more selected groups is different from a distribution of the predictor values for the trial subjects within a second group from the one or more selected groups. The statistical analysis may include calculating p-values for the statistical tests to determine whether a distribution of the predictor values for the trial subjects within one of the selected groups is different from a distribution of the predictor values for the rest of trial subjects.

In block 760, the method 700 may display, by the interactive visualization module, results of the statistical analysis. The result can be displayed in the form of a table of p-values for the predictors and in form of bar charts or histograms showing distribution of the predictors.

Figure 8:
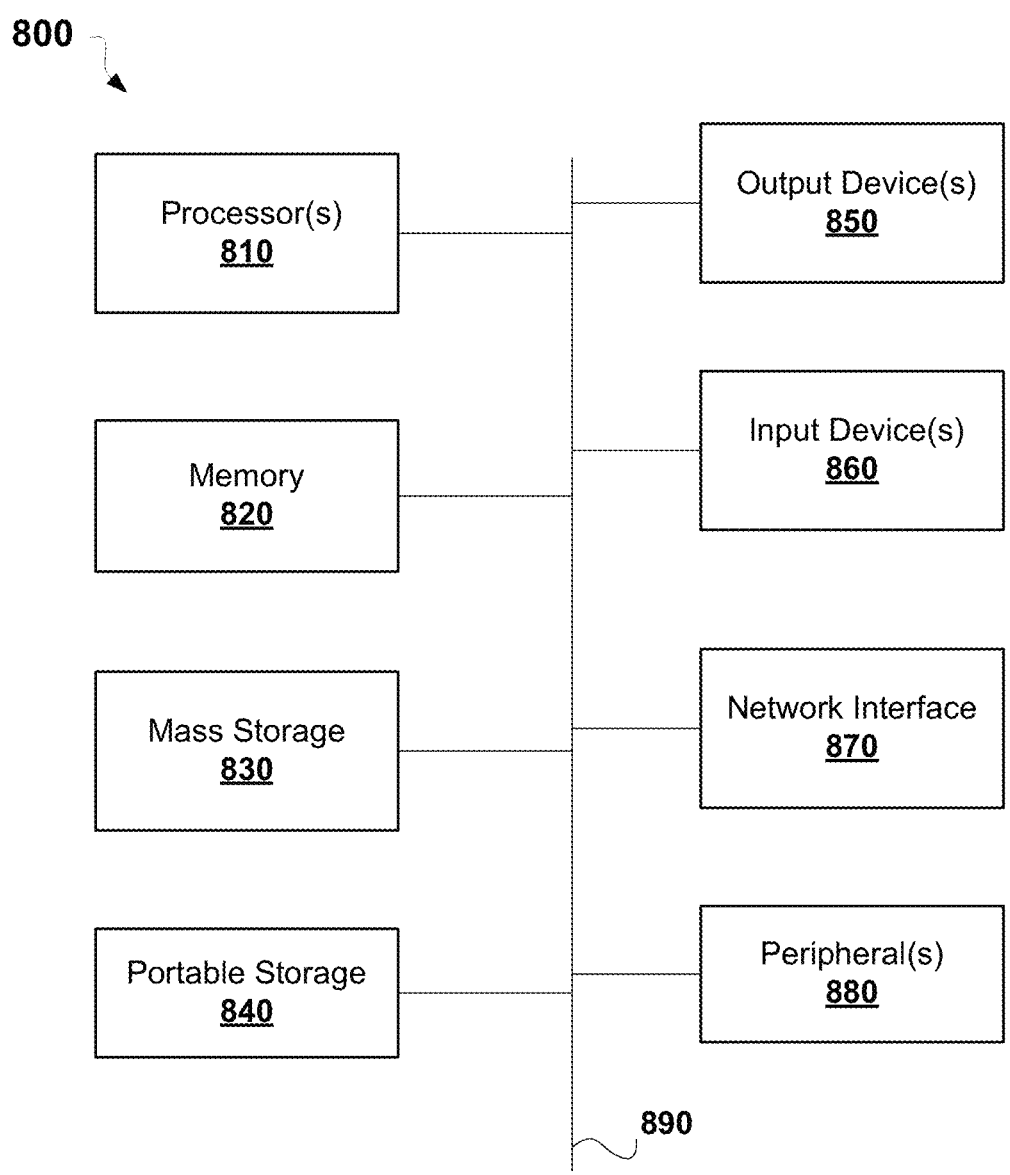
FIG. 8 is a computer system that can be used to implement the methods for topology-based clinical data mining as described herein.

FIG. 8 is a block diagram illustrating an example computer system 800 suitable for implementing the methods described herein. In particular, computer system 800 may be an instance of computer system 110, clinical datasets sources 105, or user computing device(s) 125. FIG. 8 illustrates just one example of computer system 800 and, in some embodiments, computer system 800 may have fewer components than shown in FIG. 8 or more components than shown in FIG. 8.

Computer system 800 includes one or more processors 810, a memory 820, one or more storage devices 830, a portable storage 840, one or more input devices 860, one or more output devices 850, network interface 870, and one or more peripherals 880. These components can be operatively interconnected via a communication bus 890. Processors 810 are, in some examples, configured to implement functionality and/or process instructions for execution within computer system 800. For example, processors 810 may process instructions stored in memory 820 or instructions stored on storage devices 830. Such instructions may include components of an operating system or software applications.

Memory 820, according to one example, is configured to store information within computer system 800 during operation. Memory 820, in some example embodiments, may refer to a non-transitory computer-readable storage medium or a computer-readable storage device. In some examples, memory 820 is a temporary memory, meaning that a primary purpose of memory 820 may not be long-term storage. Memory 820 may also refer to a volatile memory, meaning that memory 820 does not maintain stored contents when memory 820 is not receiving power. Examples of volatile memories include RAM, dynamic random access memories (DRAM), static random access memories (SRAM), and other forms of volatile memories known in the art. In some examples, memory 820 is used to store program instructions for execution by the processors 810. Memory 820, in one example, is used by software. Generally, software refers to software applications suitable for implementing at least some operations of the methods as described herein.

Storage devices 830 can also include one or more transitory or non-transitory computer-readable storage media and/or computer-readable storage devices. In some embodiments, storage devices 830 may be configured to store greater amounts of information than memory 820. Storage devices 830 may further be configured for long-term storage of information. In some examples, the storage devices 830 include non-volatile storage components. Examples of such non-volatile storage components include magnetic hard discs, optical discs, solid-state discs, flash memories, forms of electrically programmable memories (EPROM) or electrically erasable and programmable memories, and other forms of non-volatile memories known in the art.

Still referencing to FIG. 8, computer system 800 may also include one or more input devices 860. Input devices 860 may be configured to receive input from a user through tactile, audio, video, or biometric channels. Examples of input devices 860 may include a keyboard, keypad, mouse, trackball, touchscreen, touchpad, microphone, one or more video cameras, image sensors, fingerprint sensors, or any other device capable of detecting an input from a user or other source and relaying the input to computer system 800 or components thereof. As such, input devices 860 can be used by users or operators of system 105 to input commands, instructions, data, settings, and the like.

Output devices 850, in some examples, may be configured to provide output to a user through visual or auditory channels. Output devices 850 may include a video graphics adapter card, a liquid crystal display (LCD) monitor, a light emitting diode (LED) monitor, an organic LED monitor, a sound card, a speaker, a lighting device, a LED, a projector, or any other device capable of generating output that may be intelligible to a user. Output devices 850 may also include a touchscreen, presence-sensitive display, or other input/output capable displays known in the art. Accordingly, output devices 850 can be used to output customized reports generated by system 105.

Computer system 800, in some example embodiments, also includes network interface 870. Network interface 870 can be utilized to communicate with external devices via one or more networks such as one or more wired, wireless, or optical networks including, for example, the Internet, intranet, local area network, wide area network, cellular phone networks (e.g. GSM communications network, packet switching communications network, circuit switching communications network), Bluetooth radio, and an IEEE 802.11-based radio frequency network, among others. Network interface 870 may be a network interface card, such as an Ethernet card, an optical transceiver, a radio frequency transceiver, or any other type of device that can send and receive information.

An operating system of computer system 800 may control one or more functionalities of computer system 800 or components thereof. For example, the operating system of computer system 800 may interact with software applications of computer system 800 and may facilitate one or more interactions between the software applications and one or more of processors 810, memory 820, storage devices 830, input devices 860, and output devices 850. The operating system of computer system 800 may interact with the software applications and components thereof. In some embodiments, the software applications may be included in the operating system of computer system 800. In these and other examples, virtual modules, firmware, or software of the software applications. In other examples, virtual modules, firmware, or software may be implemented externally to computer system 800, such as at a network location. In some such instances, computer system 800 may use network interface 870 to access and implement functionalities provided by virtual modules, firmware, or software for vehicle identification through methods commonly known as "cloud computing."

Thus, the systems and methods for topology-based clinical data mining have been described. Although embodiments have been described with reference to specific example embodiments, it will be evident that various modifications and changes can be made to these example embodiments without departing from the broader spirit and scope of the present document. Accordingly, the specification and drawings are to be regarded in an illustrative rather than a restrictive sense.

What is claimed is:

1. A system for topology-based clinical data mining, the system comprising:
   at least one processor; and
   a memory storing processor-executable codes, wherein upon executing the processor-executable codes the at least one processor is configured to:
   process clinical datasets and generate:
   a first table, the first table comprising first rows representing trial subjects and first columns including outcomes of the trial subjects; and
   a second table, the second table comprising rows representing the trial subjects and columns including predictors of the trial subjects;
   generate, based on the first table, a plurality of metric graphs, wherein:
   each metric graph of the plurality of metric graphs includes a same set of nodes, each of the nodes corresponding to a single trial subject of the trial subjects in the first table; and generating a set of edges in a metric graph of the plurality of metric graphs includes:
selecting a criterion from a plurality of criteria for selectively connecting the nodes; and
selectively connecting the nodes by edges according to the selected criterion;

select, from the plurality of metric graphs and based on a further criterion, a graph of interest;

generate a compressed version of the graph of interest, the compressed version including a clustered graph;

generate a first layout of the graph of interest and a second layout of the compressed version of the graph of interest, the first layout and the second layout being visually aligned;

display, via a graphical user interface, based on one of the first layout or the second layout, a graphical representation of the graph of interest;

perform, using one or more machine learning algorithms, an automatic search to identify at least one group of related trial subjects;

highlight nodes in the graphical representation, the nodes corresponding to the related trial subjects;

receive, via the graphical representation, a user input, the user input including one or more selected groups of the trial subjects;

perform, using the second table, a statistical analysis of predictors associated with trial subjects within the one or more selected groups of the trial subjects; and display a report with results of the statistical analysis.

2. The system of claim 1, wherein the outcomes include two or more of the following: a biomarker, a vital sign, a result of physiological measurement, and a questionnaire item.

3. The system of claim 1, wherein the predictors include one or more of the following: a demographic attribute, a medical history attribute, and a medical interventions attribute.

4. The system of claim 1, wherein the at least one processor is configured to normalize data in the clinical datasets.

5. The system of claim 1, wherein the at least one processor is configured to fill in missing values for the outcomes in the first table.

6. The system of claim 1, wherein the at least one processor is configured to generate, based on the clinical datasets, one or more synthetic variables, the one or more synthetic variables being a combination of one or more outcomes associated with the trial subjects.

7. The system of claim 1, wherein the criterion includes a determination that a distance between data points corresponding to the trial subjects does not exceed a pre-determined distance threshold, the data points including vectors of the outcomes of the trial subjects.

8. The system of claim 7, wherein the distance is determined by a distance function including one of a Euclidean distance, a normalized Euclidean distance, a Manhattan distance, a Hamming distance, and a Gower distance.

9. The system of claim 1, wherein the at least one processor is configured to:
determine a graph with a highest value of an objective function of the plurality of metric graphs; and
select the graph with the highest value of the objective function as the graph of interest.

10. The system of claim 1, wherein the statistical analysis includes calculating p-values for statistical tests to determine whether a distribution of values of one of the predictors of the trial subjects within a first group from the one or more selected groups is different from a distribution of values of the one of the predictors for the trial subjects within a second group from the one or more selected groups.

11. The system of claim 1, wherein the statistical analysis includes calculating p-values for statistical tests to determine whether a distribution of values of one of the predictors for the trial subjects within the one or more selected groups is different from a distribution of values of the one of the predictors for the rest of the trial subjects.

12. The system of claim 1, wherein the at least one processor is configured to:
receive a further user input, the further user input including a selected predictor from the predictors or a selected outcome from the outcomes; and
assign colors to nodes of the graph of interest, the colors being determined based on projection values or values for the selected predictor or the selected outcome, wherein the projection values are determined based on data points including vectors of the outcomes of trial subjects corresponding to the nodes.

13. A method for topology-based clinical data mining, the method comprising:
processing, by a pre-processing module, clinical datasets to generate a first table, the first table comprising first rows representing trial subjects and first columns including outcomes of the trial subjects, and a second table, the second table comprising second rows representing the trial subjects and second columns including predictors of the trial subjects;

generating, by a graph construction module and based on the first table, a plurality of metric graphs, wherein:
each metric graph of the plurality of metric graphs includes a same set of nodes, each of the nodes corresponding to a single trial subject of the trial subjects in the first table; and
generating a set of edges in a metric graph of the plurality of metric graphs includes:
selecting a criterion from a plurality of criteria for selectively connecting the nodes; and
selectively connecting the nodes by edges according to the selected criterion;

selecting, by the graph construction module, from the plurality of metric graphs and based on a further criterion, a graph of interest;

generating, by the graph construction module, a compressed version of the graph of interest, the compressed version including a clustered graph;

generating, by the graph construction module, a first layout of the graph of interest and a second layout of the compressed version of the graph of interest, the first layout and the second layout being visually aligned;

displaying, by an interactive visualization module and based on the first layout or the second layout, a graphical representation of the graph of interest;

assigning, by the interactive visualization module, colors to the nodes of the graph of interest, wherein the colors are determined based on projection values or values of a selected outcome or a selected predictor, wherein the projections values are determined based on data points including vectors of the outcomes of trial subjects corresponding to the nodes;

performing, by the interactive visualization module and using one or more machine learning algorithms, an automatic search to identify at least one group of related trial subjects;

highlighting, by the interactive visualization module, nodes in the graphical representation, the nodes corresponding to the related trial subjects;

receiving, by the interactive visualization module and via the graphical representation, a user input including one or more selected groups of the trial subjects;

performing, by the interactive visualization module and using the second table, a statistical analysis of predictors associated with trial subjects within the one or more selected groups of the trial subjects; and displaying a report with results of the statistical analysis.

14. The method of claim 13, wherein:
the outcomes include two or more of the following: a biomarker, a vital sign, a result of a physiological measurement, and a questionnaire item; and
the predictors include one or more of the following: a demographic attribute, a medical history attribute, and a medical interventions attribute.

15. The method of claim 13, wherein processing the clinical datasets includes one or more of the following:
normalizing data in the clinical datasets;
filling in missing values for the outcomes in the first table; and
generating, based on the clinical datasets, synthetic variables, the synthetic variables representing combinations of one or more outcomes associated with the trial subjects.

16. The method of claim 13, wherein the criterion includes a determination that a distance between the data points corresponding to the trial subjects does not exceed a pre-determined distance threshold, the data points including vectors of the outcomes of the trial subjects.

17. The method of claim 13, wherein selecting the graph of interest includes:
determining a graph with a highest value of an objective function of the plurality of metric graphs; and
selecting the graph with the highest value of the objective function as the graph of interest.

18. The method of claim 13, wherein the statistical analysis includes calculating p-values for statistical tests to determine whether a distribution of values of one of the predictors for the trial subjects within a first group from the one or more selected groups is different from a distribution of the values of the one of the predictors for the trial subjects within a second group from the one or more selected groups.

19. The method of claim 13, wherein the statistical analysis includes calculating p-values for statistical tests to determine whether a distribution of values of one of the predictors for the trial subjects within a group from the one or more selected groups is different from a distribution of values of the one of the predictors for the rest of the trial subjects within the clinical datasets.

20. A system for topology-based clinical data mining, the system comprising:
at least one processor; and
a memory storing processor-executable codes, wherein upon executing the processor-executable codes the at least one processor is configured to:
process clinical datasets to generate a first table, the first table comprising first rows representing trial subjects and first columns including outcomes of the trial subjects, and a second table, the second table comprising second rows representing the trial subjects and second columns including predictors of the trial subjects;

generate, based on the first table, a plurality of metric graphs, wherein:
each metric graph of the plurality of metric graphs includes a same set of nodes and edges, each of the nodes corresponding to a single trial subject of the trial subjects in the first table; and
generating a set of edges in a metric graph of the plurality of metric graphs includes:
selecting a criterion from a plurality of criteria for selectively connecting the nodes; and
selectively connecting the nodes by edges according to the selected criterion;

estimate values of an objective function of the plurality of metric graphs;

select, from the plurality of metric graphs and based on the values of the objective function, a graph of interest;

generate a compressed version of the graph of interest, the compressed version including a clustered graph;

generate a first layout of the graph of interest and a second layout of the compressed version of the graph of interest, the first layout and the second layout being visually aligned;

display, via a graphical user interface, based on one of the first layout and the second layout, a graphical representation of the graph of interest;

assign, based on projection values or values for a selected predictor or a selected outcome, colors to the nodes of the graph of interest, wherein the projection values are determined based on data points including vectors of the outcomes of the trial subjects corresponding to the nodes;

perform, using one or more machine learning algorithms, an automatic search to identify at least one group of related trial subjects;

highlight nodes in the graphical representation, the nodes corresponding to the related trial subjects;

receive, via the graphical representation, a user input, the user input including one or more selected groups of the trial subjects; and perform, using the second table, a statistical analysis of predictors associated with the trial subjects, wherein the statistical analysis includes one of:
calculating p-values for statistical tests to determine whether a distribution of values of one of the predictors for the trial subjects within a first group from the one or more selected groups is different from a distribution of values of the one of the predictors for the trial subjects within a second group from the one or more selected groups;
calculating p-values for the statistical tests to determine whether a distribution of values of the one of the predictors for the trial subjects within a group from the one or more selected groups is different from a distribution of values of the one of the predictors for the rest of the trial subjects within the clinical datasets; and
displaying results of the statistical analysis.

\* \* \* \* \*